US008617098B2

(12) United States Patent
Gerber

(10) Patent No.: US 8,617,098 B2
(45) Date of Patent: *Dec. 31, 2013

(54) RETROFITTABLE ASPIRATION PREVENTION MECHANISM FOR PATIENTS

(76) Inventor: Allen Gerber, High Falls, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/422,974

(22) Filed: Mar. 16, 2012

(65) Prior Publication Data

US 2012/0191038 A1 Jul. 26, 2012

Related U.S. Application Data

(63) Continuation-in-part of application No. 12/070,515, filed on Feb. 19, 2008, which is a continuation-in-part of application No. 11/804,109, filed on May 17, 2007, which is a continuation-in-part of application No. 11/545,382, filed on Oct. 10, 2006, now Pat. No. 7,833,188.

(51) Int. Cl.
A61M 31/00 (2006.01)

(52) U.S. Cl.
USPC .......................................... 604/67

(58) Field of Classification Search
USPC .............................. 604/65, 66, 67
See application file for complete search history.

(56) References Cited

U.S. PATENT DOCUMENTS

| 4,348,562 | A | * | 9/1982 | Florin | 200/52 R |
| 5,611,096 | A | * | 3/1997 | Bartlett et al. | 5/617 |
| 7,487,562 | B2 | * | 2/2009 | Frondorf et al. | 5/613 |
| 7,562,458 | B1 | * | 7/2009 | Clark et al. | 33/333 |
| 7,594,286 | B2 | * | 9/2009 | Williams | 5/424 |
| 7,833,188 | B2 | * | 11/2010 | Gerber | 604/67 |
| 7,967,780 | B2 | * | 6/2011 | Goebel | 604/100.01 |
| 8,021,322 | B1 | * | 9/2011 | Francis | 604/66 |
| 2006/0021240 | A1 | * | 2/2006 | Horgan | 33/366.11 |
| 2006/0154642 | A1 | * | 7/2006 | Scannell, Jr. | 455/404.1 |
| 2007/0143920 | A1 | * | 6/2007 | Frondorf et al. | 5/81.1 R |
| 2007/0268480 | A1 | * | 11/2007 | Kaye | 356/138 |
| 2008/0086076 | A1 | * | 4/2008 | Gerber | 604/43 |
| 2008/0146994 | A1 | * | 6/2008 | Gerber | 604/66 |
| 2008/0154191 | A1 | * | 6/2008 | Gobel | 604/101.05 |
| 2008/0171963 | A1 | * | 7/2008 | Gerber | 604/19 |
| 2009/0299229 | A1 | * | 12/2009 | Johnson et al. | 600/587 |
| 2010/0060569 | A1 | | 3/2010 | Shamilian | |

(Continued)

FOREIGN PATENT DOCUMENTS

KR 10-2012-0004579 A 1/2012

OTHER PUBLICATIONS

International Search Report and Written Opinion dated Jul. 18, 2013 for PCT/US2013/031465.

Primary Examiner — Aarti B Berdichevsky
(74) Attorney, Agent, or Firm — Leason Ellis LLP.

(57) ABSTRACT

A device is employed that can be retrofit onto existing feed pumps to remediate the problem of fluid aspiration in patients being fed through a feeding tube from the pump. In one embodiment the feeding pump is plugged into the device which is plugged into a power outlet. A patient angle sensor triggers power cutoff to the pump and stoppage of fluid flow. The angle sensor and operating program may be part of a smart phone. Power to the pump may be shut off due to a BLUETOOTH® signal from the smart phone to a BLUETOOTH® controlled power strip into which the pump is plugged to receive power.

28 Claims, 13 Drawing Sheets

(56) References Cited

U.S. PATENT DOCUMENTS

| | | | |
|---|---|---|---|
| 2011/0015611 A1* | 1/2011 | Gerber | 604/500 |
| 2011/0137213 A1* | 6/2011 | Caulfield et al. | 600/595 |
| 2011/0234395 A1* | 9/2011 | Johnson et al. | 340/539.12 |
| 2012/0191038 A1 | 7/2012 | Gerber | |

* cited by examiner

RETROFITTABLE ASPIRATION PREVENTION MECHANISM FOR PATIENTS

CROSS-REFERENCE TO RELATED APPLICATIONS

The present application is a continuation-in-part application of patent application Ser. No. 12/070,515 filed on Feb. 19, 2008, which is itself a continuation-in-part of patent application Ser. No. 11/804,109 filed on May 17, 2007, which is itself a continuation-in-part of patent application Ser. No. 11/545,382 filed on Oct. 10, 2006 (now U.S. Pat. No. 7,833, 188 issued on Nov. 16, 2010). This application contains subject matter which is related to the subject matter of the above-mentioned applications, which is owned by the same entity as the present application.

TECHNICAL FIELD

The present invention is generally directed to the medical field as it relates to patient care, particularly in a hospital, nursing home or other institutional settings and even in some home care settings. More particularly, the present invention relates in general to systems and methods for preventing aspiration of stomach contents by bed ridden patients connected to feeding tubes and to ancillary functions that may be performed by such devices.

BACKGROUND OF THE INVENTION

It is well known that millions of people around the world are fed through gastric feeding tubes once they can no longer feed themselves. The most common version of this practice occurs in the use of nasogastric feeding tubes. Other gastric feeding practices include the surgical insertion of a feeding tube directly into the stomach through the abdominal wall (PEG tubes). The present invention is employable in all of these situations in which gastric feeding is provided. Thus, in the appended claims the term gastric tube refers to both nasogastric tubes and to PEG tubes.

While the use of gastric feeding mechanisms is not only a common and a life preserving procedure, complications can arise. In particular, one of these complications is aspiration pneumonia. This condition can be life threatening, particularly in older patients with decreased gag reflexes, or patients who have suffered a stroke, have a decreased level of consciousness from a drug overdose, are post-surgical or have weakened immune systems. A common one of these mechanisms is one in which the patient slides down in bed to an angle which is sufficiently to allow gastric fluids to ascend the esophagus and to be inhaled into the lungs. Typically, this angle is about 30.degree. When the patient angle in the bed reaches this point, the stomach contents are able to percolate up through the esophagus and down into the lungs. The fact that this is a significant problem in patient care is reflected in the fact that in many states the occurrences of aspiration pneumonia resulting in death are reportable incidents to state oversight authority. The importance of preventing aspiration pneumonia is further reflected by the fact the Inspector General's report of November 2010 has classified this as a potential preventable event. The importance of this issue is further seen in the fact that all hospitals and health care facilities in the Unites States have internal policies that mandate that the patient be keep at greater than 30° while being feed through a tube. These internal policies are the result of recommendations from the Center for Disease Control, the Joint Commission, and the American Society for Parenteral and Enteral Nutrition (A.S.P.E.N.). Still further evidence of the importance of this issue is that there are thousands of preventable deaths and the loss of billions of healthcare dollars in the United States each year. The reversal of this deplorable situation is a current mandate of Congress.

The use of feeding pumps has been around for several decades. However, the problem of aspiration, while it has been around as long as the use of such devices, has not been addressed by the medical instrumentation arts which have failed to address the problems associated with the use of feeding tubes, feeding pumps and the problems of aspirated materials. The present invention provides a simple device which can be used to retrofit existing feed pumps and which is simple, inexpensive and easy to operate, whether or not implemented using microprocessor control.

It is noted that, while the present invention is principally directed to the problems associated with gastric feeding tubes, nonetheless, it is equally applicable to those situations in which substances other than nourishment are being provided through such a tube.

From the above, it is therefore seen that there exists a need in the art to overcome the deficiencies and limitations described herein and above.

SUMMARY OF THE INVENTION

Accordingly, in order to solve these problems, there is provided a mechanical or electronic device that senses when a patient slides down below a predetermined angle. The device is operable in one of two ways or in both ways. In a first embodiment, the detection of improper patient angle shuts off power being supplied to the feeding device. This embodiment is implemented by interposing a controllable power switch between an electrically powered feeding pump and the A/C wall outlet or other source from which the pump is being powered. In a second embodiment of the present invention, the detection of improper patient angle triggers a motor, relay, or solenoid with a mechanical actuator which squeezes the feeding tube with sufficient pressure to stop the flow of material within the tube. This latter modality of operation is best suited for use with pumps that include a battery backup for purposes of safety during power failures.

In preferred embodiments of the present invention, the device is controlled via a microprocessor. The use of a microprocessor provides the ability to more closely monitor and detect patient activity, control an angle sensor and provide additional functions, such as determining that a patient has fallen below a pre-set angle where safe feeding is assured. In one preferred embodiment the microprocessor is contained in a "smart phone" such as the APPLE® iPhone®. The smart phone can be attached to the chest of the patient, e.g., by placing it in a breast pocket of the patient's pajamas, and the determination of the inclination of the patient can be made by an accelerometer application running on the smart phone under the control of its microprocessor. In order to implement the present invention, a second application is especially designed for the smart phone. This application monitors the patient inclination information from the accelerometer application and generates a signal when it indicates, e.g., that the patient's angle is nearing or below 30°. This special application then triggers a wireless communications device, e.g., a BLUETOOTH® circuit, in the smart phone and causes it to generate a wireless BLUETOOTH® signal. The feeding pump is plugged into a wireless, e.g., BLUETOOTH®, controlled power strip so that when the special application generates the critical angle signal, power in the strip is cut off and the pump stops. Further, the special application in the smart phone may be programmed to sound an alarm in the smart phone and/or to use the phone circuits in the smart phone to call a nurse's station and to indicate that the pump has stopped. In this way existing feeding pumps can be retrofitted to employ the present invention without making any changes to the existing pumps or constructing specialized hardware devices.

The sensing of patient position below a certain angle may also be used to alert the attending medical staff that a patient is in an undesirable position. Additionally, the detection of an undesirable patient angle may also be employed to automatically raise the head and/or foot portion of an adjustable bed so as to prevent further downward sliding.

Additional features and advantages are realized through the techniques of the present invention. Other embodiments and aspects of the invention are described in detail herein and are considered a part of the claimed invention.

Accordingly, it is an object of the present invention to reduce and/or eliminate the problem of aspiration in patients connected to gastric tubes.

It is also an object of the present invention to reduce and/or eliminate the problem of exposing portions of the esophagus to gastric fluids.

It is a still further object of the present invention to provide medical staff with an indication of undesired patient movement.

It is yet another object of the present invention to provide a feedback mechanism for raising the foot portion of a patients bed to prevent further sliding.

Additional features and advantages are realized through the techniques of the present invention. Other embodiments and aspects of the invention are described in detail herein and are considered a part of the claimed invention.

The recitation herein of desirable objects which are met by various embodiments of the present invention is not meant to imply or suggest that any or all of these objects are present as essential features, either individually or collectively, in the most general embodiment of the present invention or in any of its more specific embodiments.

BRIEF DESCRIPTION OF THE DRAWINGS

The subject matter which is regarded as the invention is particularly pointed out and distinctly claimed in the concluding portion of the specification. The invention, however, both as to organization and method of practice, together with the further objects and advantages thereof, may best be understood by reference to the following description taken in connection with the accompanying drawings in which:

DETAILED DESCRIPTION

Figure 1:
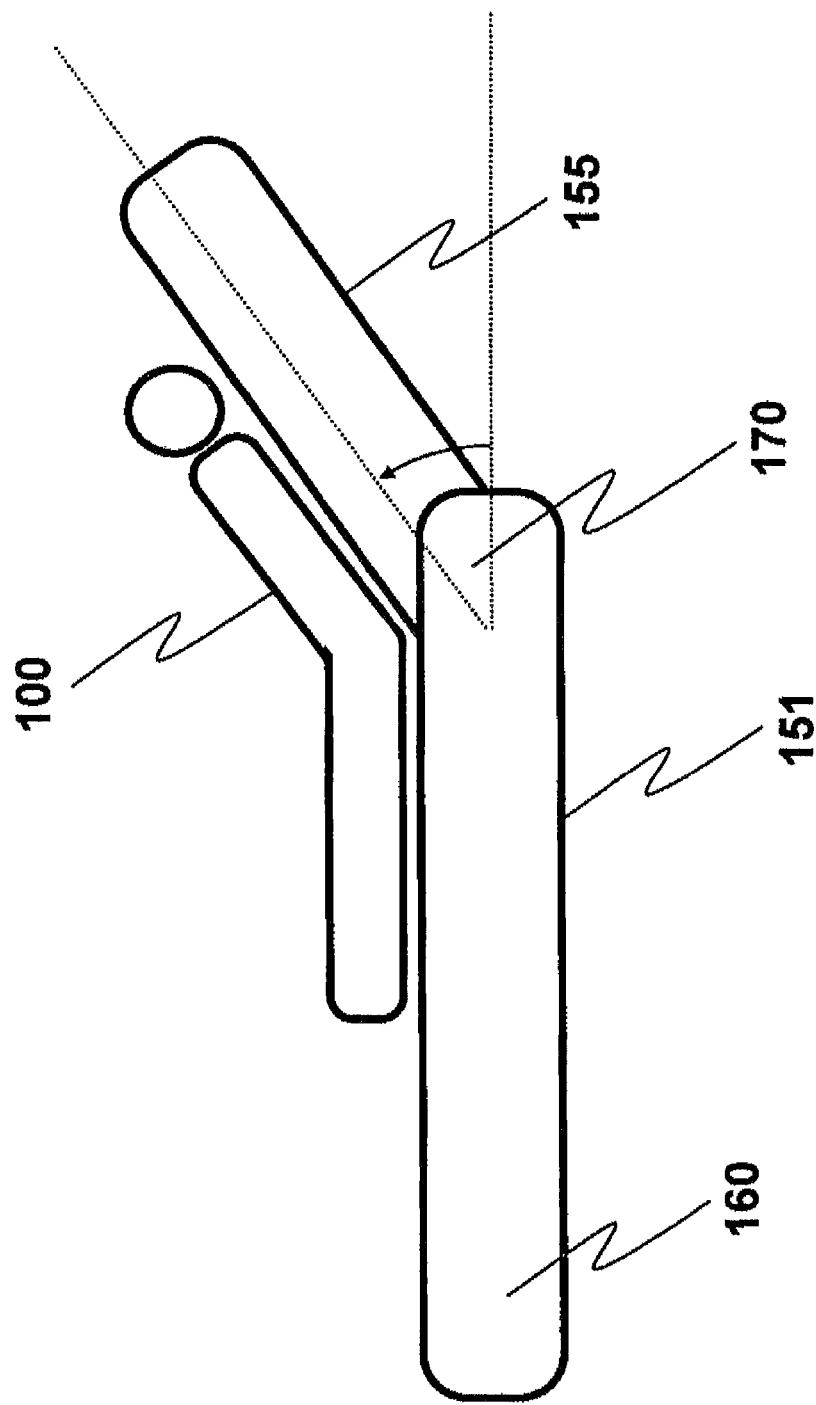
FIG. 1 is a side elevation view indicating the relative positions of a patient and a bed with a head part that reclines, and particularly indicating the angle of the bed.

FIG. 1 illustrates the environment in which the present invention is employed. In particular, there is shown patient 100 positioned in a reclining position on bed 150 which includes movable head portion 155 and which may also include a likewise movable foot portion 160 which is employed either for patient comfort or for elevation of the lower extremities. It is also seen the patient is reclining at angle 170 with respect to the horizontal. Reference to the horizontal is employed herein for measurement and determination of improper angle since the "horizontal" is really determined by gravity and it is gravity that is the principal driver of gastric fluid into the esophagus and lung.

It is noted herein that the angle shown in FIG. 1 is the angle of the adjustable head portion of the bed with respect to the horizontal portion of the bed. Even though the illustration suggests it, FIG. 1 does not reflect the fact that the position of a patient who has slid down in the bed. It should also be noted that the beds of concern herein may also be equipped with adjustable foot portion 160 as well. In fact, if it is detected that patient 100 is sliding down in the bed; the adjustable foot portion of the bed may be raised to prevent further sliding. This is an optional feature of the present invention.

Figure 2:
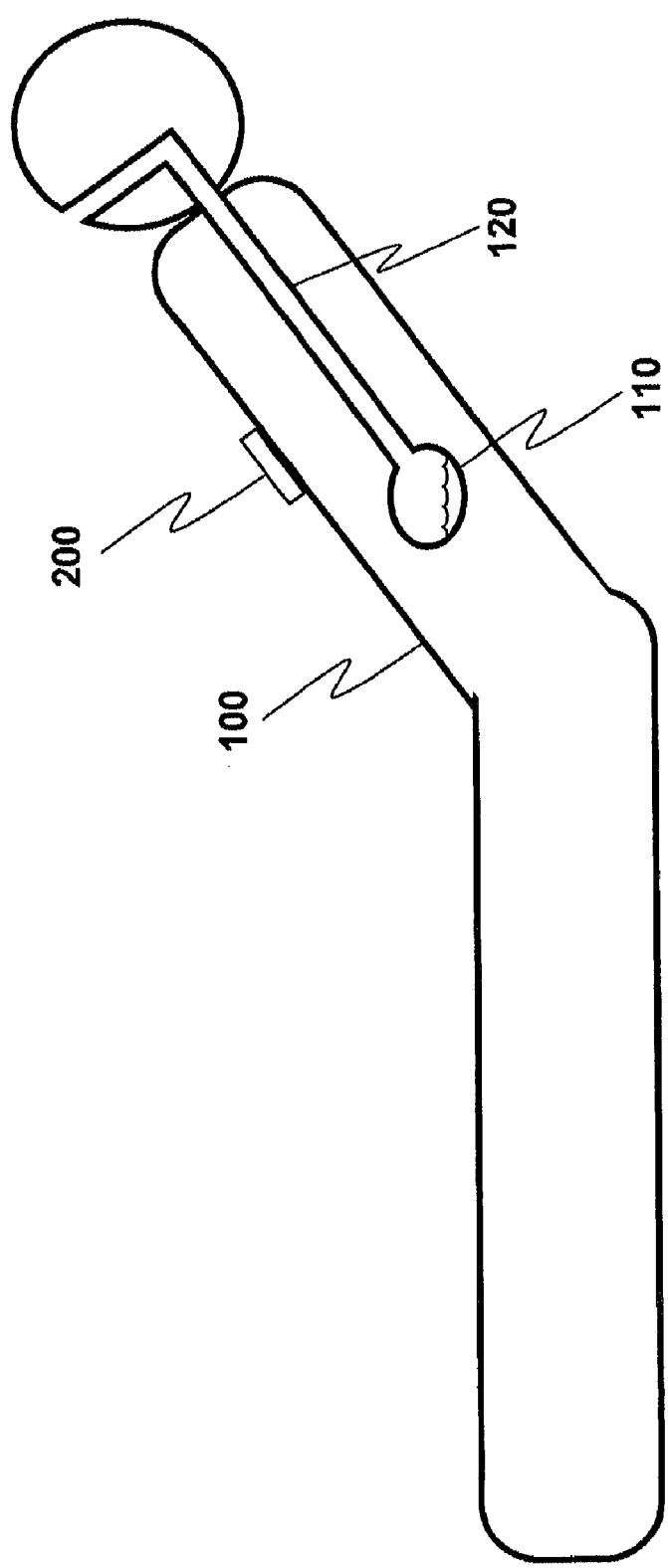
FIG. 2 is a stylized, side elevation view of a patient showing the stomach and esophagus for a patient reclining at the angle shown in FIG. 1, as well as showing the placement of an angle sensor.

FIG. 2 provides a greater detail of the situation being considered with respect to patient 100 and the specific problem that is solved. Basic human anatomy teaches that stomach 110 is connected to esophagus 120. It is easily seen that if the patient's angle is low, that is, if the patient is closer to a horizontal position, stomach contents can enter esophagus 120 simply by gravity flow. The problems associated with this flow are discussed above, but, needless to say, it is not a desirable situation.

Additionally, FIG. 2 illustrates the placement of sensor 200. Sensor 200 is preferably placed on the chest of patient 200. It is affixed to the patient or to the patient or to the patient's clothing by any convenient means (though the latter is not preferred since clothing position is not always a good indicator of patient angle or position). For short term use adhesive material on one side of sensor 200 holds it in place. For use with clothing or gowns, a wider range of options is available for affixing the sensor, including pins, elastic bands and VELCRO®, These latter two items may also be employed to affix the sensor more firmly to the patient. Sensor 200 comprises any convenient mechanism for sensing angle. At its simplest it comprises a mercury filled insulative container with electrical contacts being closed when it contact with the mercury. The interior shape of the container is such that the mercury becomes in contact with the contacts at a predetermined angle. The sensor may also include adjustable exterior flaps to provide a selectable angle. It is noted, however, that there is a wide range of sensors and sensor technology which may be employed. For example, one could employ a ball or other sliding or rolling interior object which either makes electrical contact or which is of sufficient weight to cause switch contacts to close. Additionally, the interior moving object may be employed to interrupt light falling on a photocell. Magnetic or other optical sensors may be employed as well. In fact, any device which implements the generation of an electrical or even electromagnetic signal based on dependence on an angle with respect to feeding tube flow is employable. As indicated, the sensor may even comprise a wireless device which transmits an activation signal to pump control 220. More sophisticated sensors 200 which actually provide a signal indicative of the actual angle, as opposed to the angle merely exceeding a threshold value are also employed in the present invention. With a more sophisticated indication of angle being provided, it is then possible to provide an early warning indication of a patient sliding downward. In such cases, the alarm to patient or staff is variable in intensity depending on the angular degree sensed.

Figure 3:
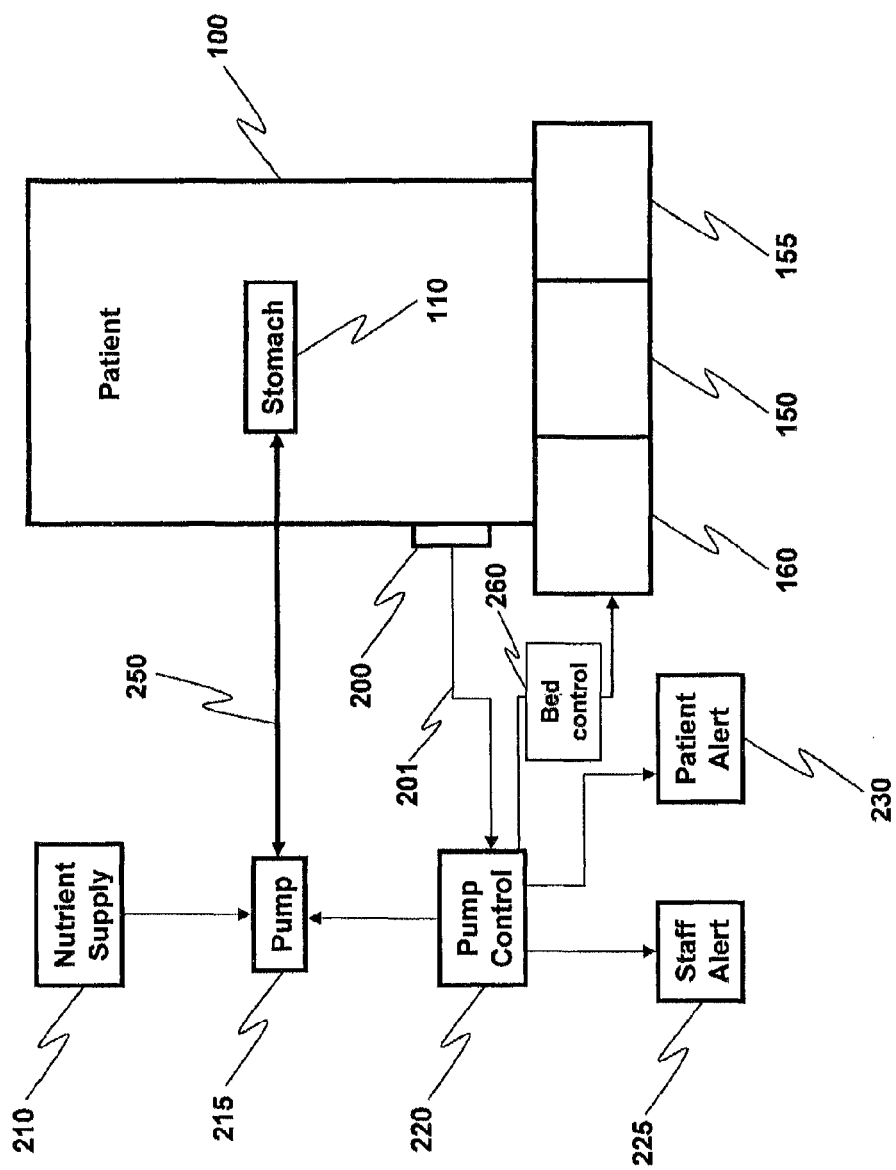
FIG. 3 is a block diagram illustrating the system and method of the present invention.

The solution to the aspiration problem is shown in greater detail in FIG. 3. In particular, sensor 200, which is affixed to patient 100, sends a signal to pump control 220 which, in normal operation, sends nutrient materials from supply 210 to stomach 110 of patient 100. If patient 100 slides down in bed 150 to an undesired, predetermined angle, sensor 200 signals pump control 220 to shut off the supply of nutrient or other material to stomach 110. Additionally, the system is provided with an optional feature in which gastric fluid is actually pulled back into gastric tube 250. In this regard, note the two directions indicated for tube 250.

It is also seen that the signal from sensor 200 is also capable of providing an audible or visual signal 225 to hospital staff members to alert them that patient 100 has slid down into bed 150 to an undesirable and possibly unsafe position. Pump control 220 may also be used to supply an audible, visual or vibratory signal 230 to patient 100 as a mechanism for immediate correction by the patient himself or herself, if possible. This same signal from sensor 200 may also be used to control bed 150. In particular, in conjunction with a bed control unit (not shown), sensor 200 is also seen to be capable of providing an actuation signal to cause foot portion 160 of bed 150 to raise so as to forestall further sliding.

In the discussion above, it is assumed that nutrients are provided through a gastric tube via a pump which acts as a positive control element in the system. However, it is noted that it is also possible that nutrient supply 210 may be positioned above the patient so that it is supplied by gravitational action. In this case, the role of "pump" 220 is less "active" in that it operates not so much as a pump but as a valve to control the rate of flow. In such an arrangement the optional feature of pump reversal is not available. However, apart from this drawback, the present invention is equally capable of operating with gravity flow systems.

Figure 8:
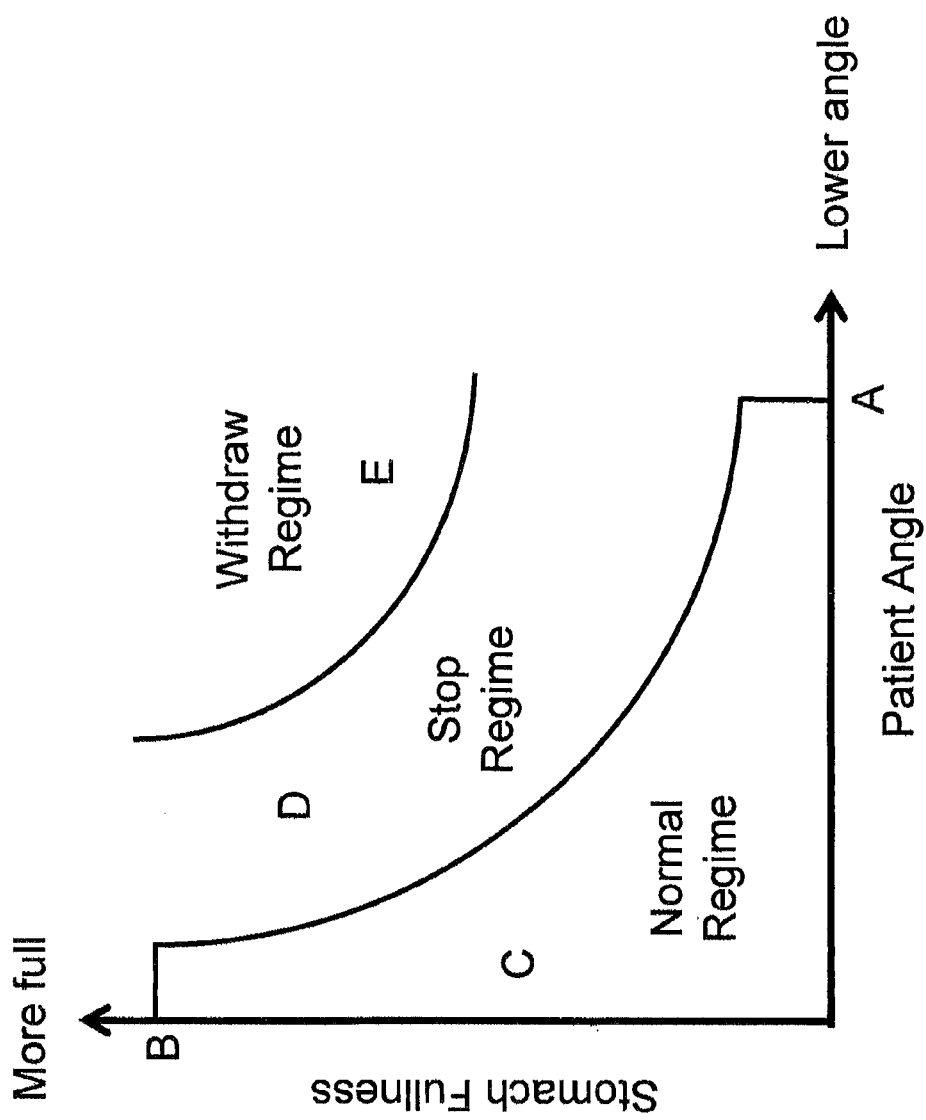
FIG. 8 is a diagram illustrating an exemplary flow control algorithm based on both patient angle and fullness sensor.

Pump control 220 is provided by any convenient mechanism. Application specific integrated circuit (ASIC) chips may be employed, off-the shelf control components may be used or pump control 220 may be implemented via any standard microprocessor or microcontroller. An exemplary control algorithm based on sensed patient angle and patient stomach content level is shown in FIG. 8.

Figure 4:
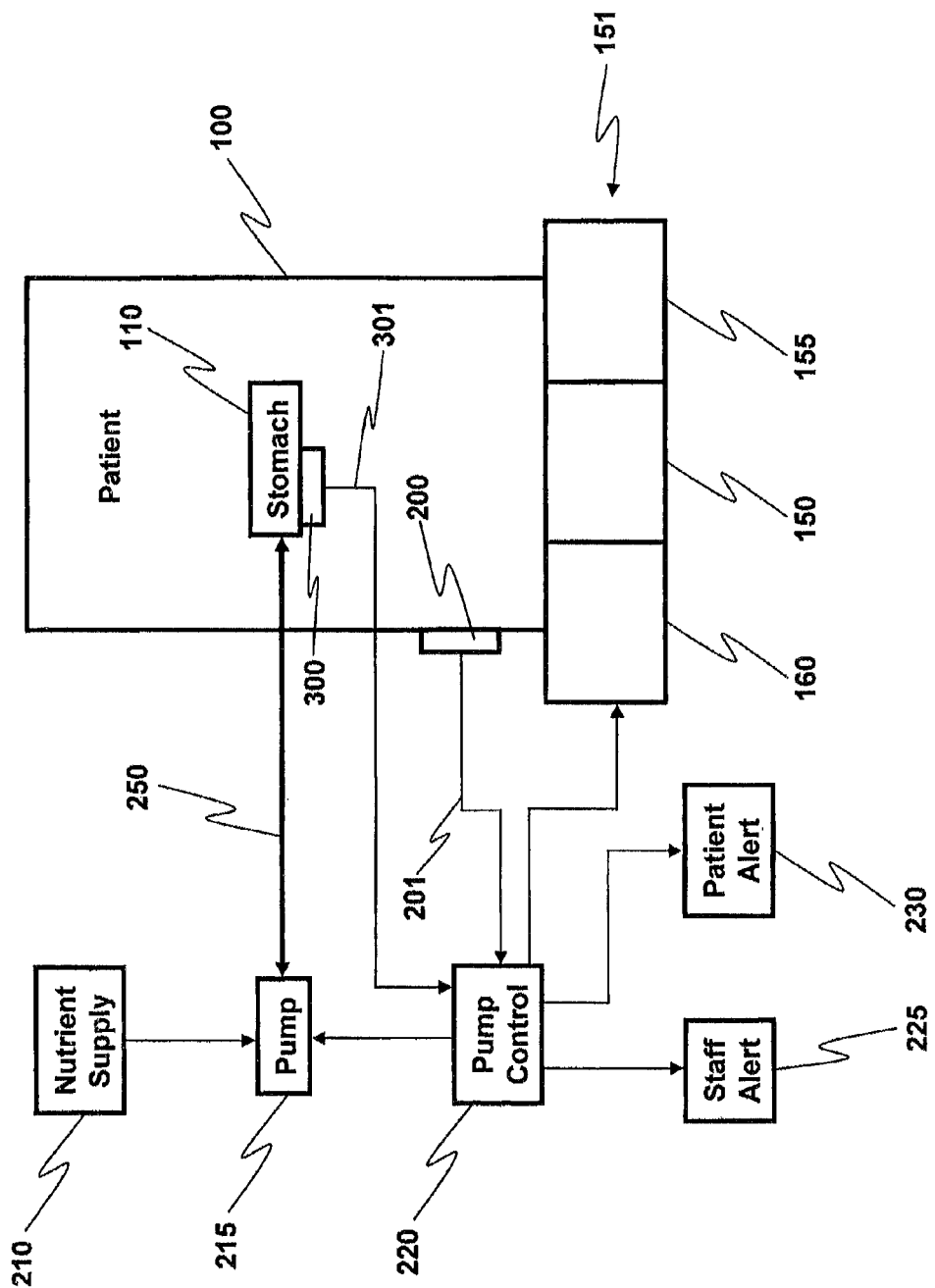
FIG. 4 is a block diagram view similar to FIG. 3 but more particularly illustrating the presence of a stomach content quantity sensor.
Figure 5:
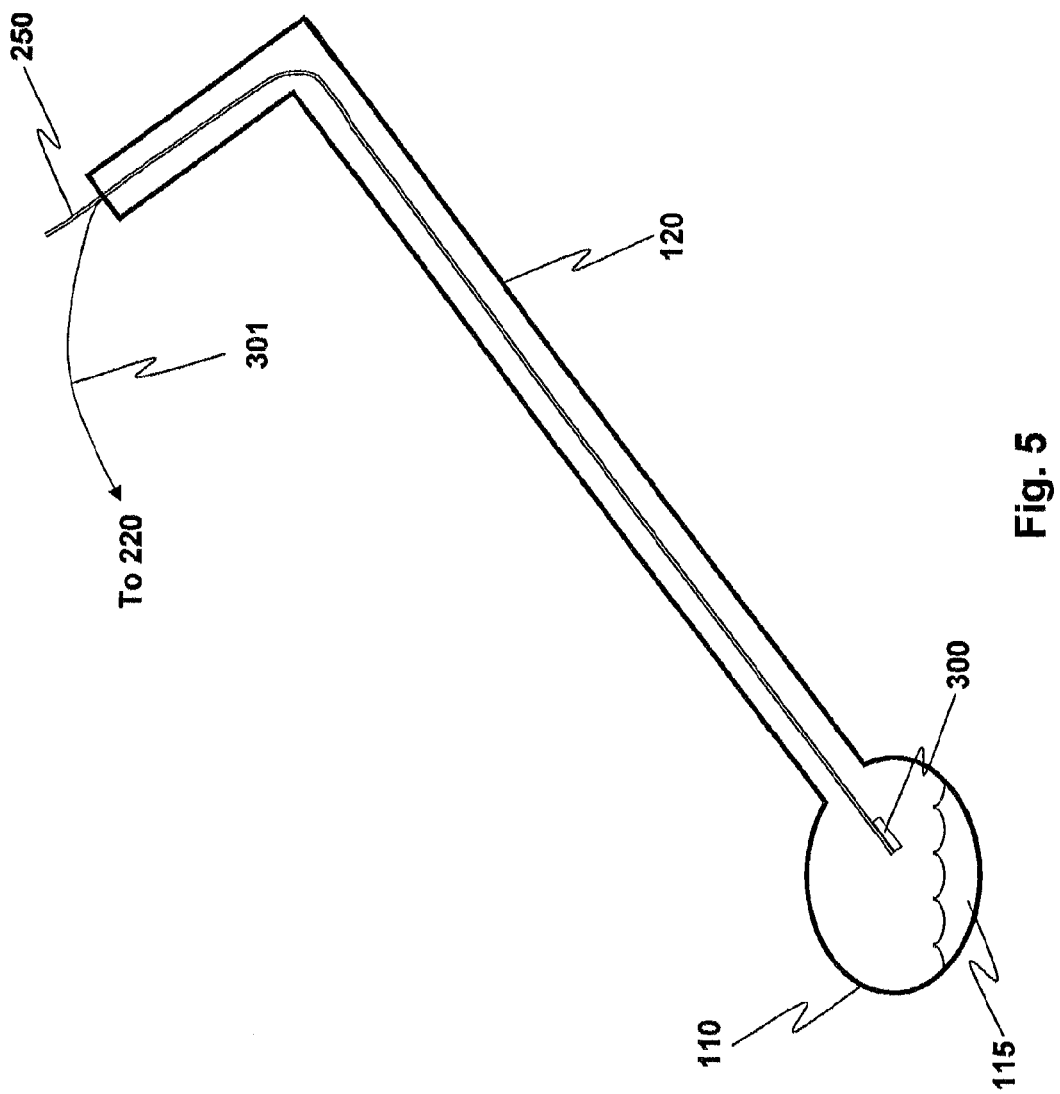
FIG. 5 is an enlarged view of a portion of FIG. 2, which more particularly illustrates an embodiment of the present invention employing a stomach content sensor.

FIG. 4 is similar to FIG. 3 but it more particularly illustrates the presence of an additional mechanism which is capable of providing an indication of the quantity of material within the stomach at any given time. In particular, one form of fullness sensor 300 is disposed at the end of feeding tube 250 as shown in FIG. 5. When implemented in this fashion, fullness sensor 300 has connected thereto signal wire or cable 301 which is typically disposed alongside feeding tube 250 or may be manufactured along with it as an integral assembly. Wire or cable 301 is provided to pump control 220 to be used, either alone or in conjunction with a signal from angle sensor 200, to control the flow of fluid in feeding tube 250, either stopping it, or in some cases, actually reversing the flow.

Fullness sensor 300, as shown in FIG. 5 may comprise an electrical circuit whose properties change when in contact with gastric fluid 115. Fullness sensor 300 may also respond to being in contact with any liquid; it may respond to being in contact with a liquid of a certain acidity; or fullness sensor 300 may respond to the level of liquid present. Additionally, fullness sensor 300 may also include ultrasonic transmission and receiving components which produce a signal which is proportional to or a function of unoccupied gastric volume. In this way, if a known volume of fluid is introduced into the stomach in a known amount of time, ultrasonic fullness sensor 300 provides "before" and "after" signals which can be used to indicate the change in stomach volume as a percentage which occurs as the result of the input of a known volume in a known amount of time. In this way, stomach volume can be calculated and the sensor can be calibrated accordingly. Fullness sensor 300 may also comprise a pressure transducer which responds to elevated levels of gas pressure within the stomach.

Exterior ultrasound measurements produced using readily available equipment may also be employed as a mechanism for determining fullness and the need to either stop or withdraw fluid. This approach, however, typically has the disadvantage of requiring human intervention and is harder to automate.

Figure 6:
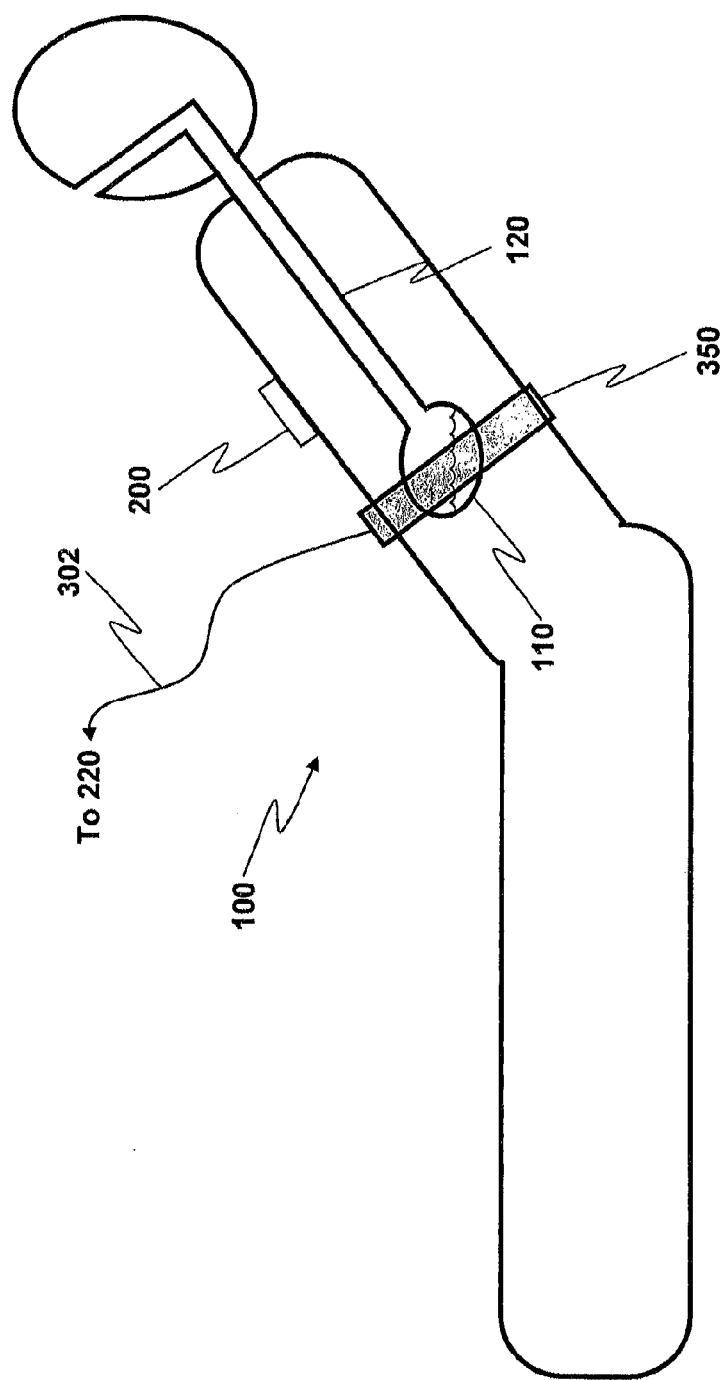
FIG. 6 is a schematic diagram illustrating the use of a girth sensor for providing a fullness signal.

FIG. 6 illustrates the situation in which girth sensor 350 is employed as a mechanism for determining stomach fullness and/or changes in stomach fullness. Girth sensor 350 is disposed about the patient's abdomen as shown and lead 302 is supplied to pump control 220. In the event that girth sensor 350 includes a wireless transmission device, electrical conductor 302 is not necessary.

Figure 7:
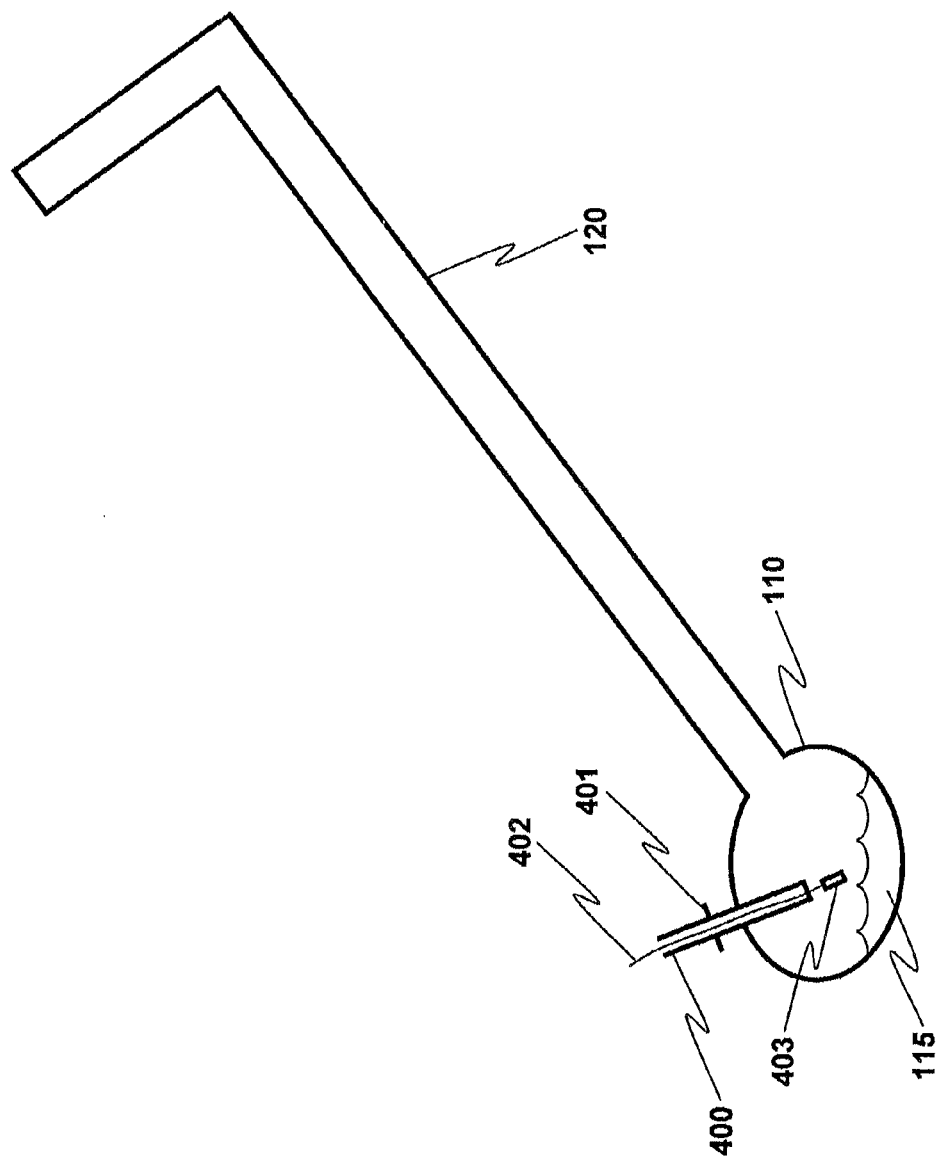
FIG. 7 is a schematic diagram similar to FIG. 5 but more particularly illustrating the use of a PEG tube.

FIG. 7 illustrates the use of the present invention when, instead of a nasogastric tube, PEG tube 400 is employed. Such tubes typically include collar portion 401 which is disposed against the abdomen and is affixed thereto in a sealed fashion to guard against providing a passage for infection. Fullness sensor 403 is disposed through PEG tube 400 and is coupled externally through electrical conductor 402.

FIG. 8 represents an exemplary algorithm for pump control and/or stoppage control (the latter being especially in the case of a gravity driven nutrient supply) based jointly on patient angle and patient stomach fullness. In the case of each variable, it is seen that there is a point reached where some action is taken such as when the patient angle gets too low (point A in FIG. 8) or when the patient's stomach contents become too full (point B), this latter point being particularly desirable in the implementation of a method designed to keep stomach contents out of the esophagus, independent of patient angle. Also shown in FIG. 8 is region C which illustrates normal operation in a region of relatively high patient angle and low stomach contents. As these variables change in a direction away from the illustrated origin, control enters a control regime D in which feeding or nutrition flow is stopped. Further excursions of these variables in a direction away from the indicated origin result in flow control entering region E characterized not just by flow stoppage but by flow reversal. As should be fully appreciated, variations of the regions illustrated in FIG. 8 are not only possible to achieve specific purposes in particular patients but it is also easily possible to implement any diagram such as that shown using microprocessors with the given curves stored in its memory in a number of convenient forms.

The present invention is preferably provided with a dual axis accelerator and/or inclinometer such as the ADIS 16003 model as provided by Analog Devices, Inc. In this regard, it is noted that patient angle sensors per se appear to have been described in U.S. Pat. No. 4,348,562 issued to Robert E. Florin and issued on Sep. 7, 1982. However, the use of this angle sensor is limited to the detection of conditions leading to patient falls. Since the present invention includes the use of a controller and a more sophisticated sensor, the present invention preferably also includes an alarm function unrelated to the desire to halt the flow of fluid in a feeding (or other) tube. For example, it is known that patients sometimes aspirate food, phlegm or saliva even if they are not currently being fed with a feeding tube. In those circumstances in which a feeding tube is disconnected, even temporarily, the present invention is still preferably kept in place to monitor patient angle to prevent aspiration of material unrelated to the feeding tube situation. This is particularly true for stroke patients, but for many other types of patients as well.

Figure 9:
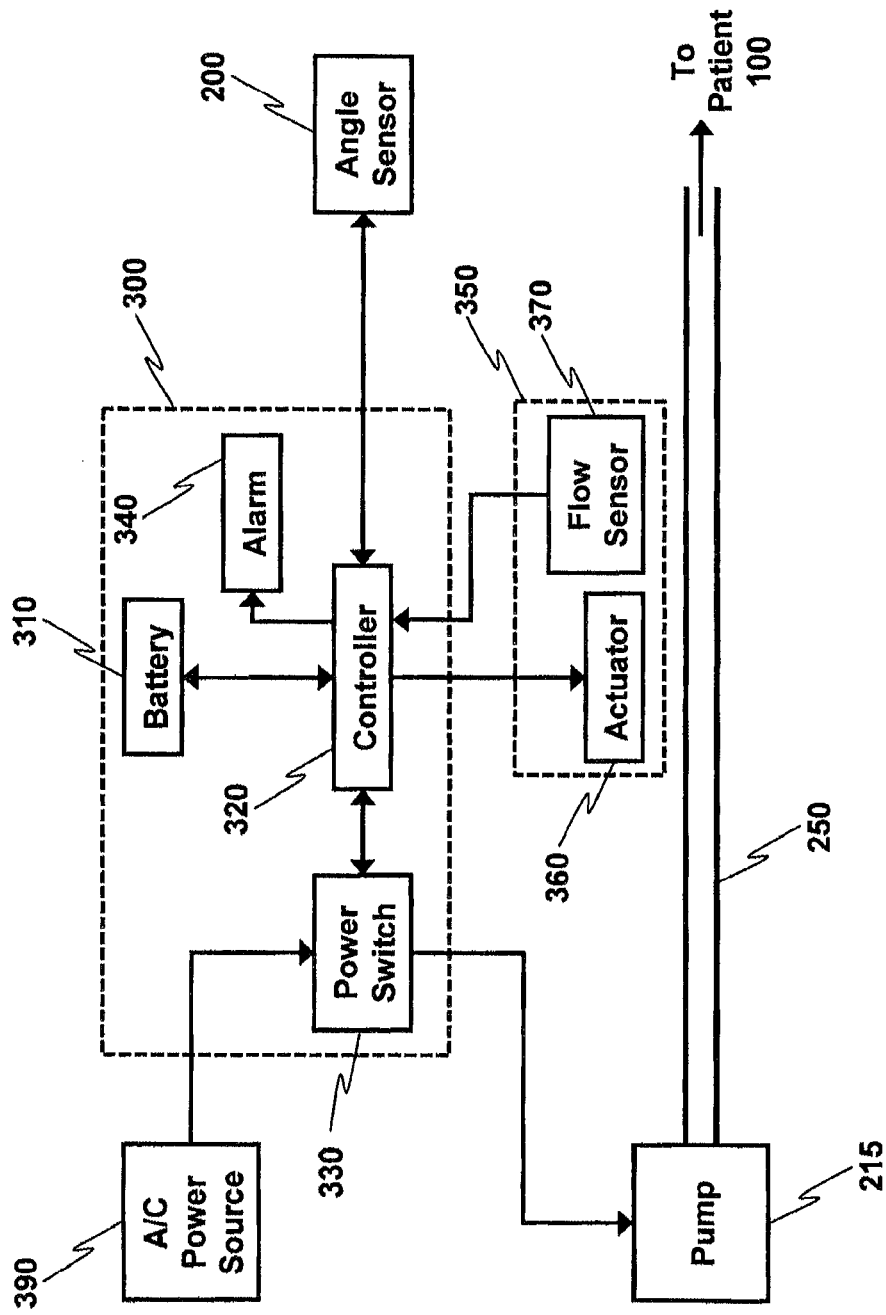
FIGS. 9 and 10 are block diagrams illustrating the various components of the present invention, with FIG. 10 illustrating a wireless version.

FIG. 9 illustrates an embodiment of the present invention which can be retrofit to work with and/or used in conjunction with currently available feeding pumps and related devices. In particular, it is seen that the embodiment shown in FIG. 9 shows the invention as main package 300 which is for example plugged into source of electrical power 390. Pump 215, which is to be controlled by the present invention, it is then preferably connected to an electrical outlet interface provided on main package 300. Two other connections are made to package 300 in the deployment of the present invention. In particular, angle sensor 200 is disposed attached to an electrical cable which also plugs into package 300. Package 300 further includes any convenient form of pluggable electrical cable for connecting to actuator 360 disposed in separate package 350 which optionally also includes flow sensor 370. Actuator 360 is disposed so as to at least partially surround feeding tube 250 and which is activated by controller 320 to squeeze tube 250 to prevent further flow of nutrients or medication to patient 100. It should also be understood that sensor 200 and controller housing 300 may be provided as a single integrated component. However, in such cases it is desirable that A/C power level components such as power switch 330 be disposed outside of this housing.

Package 300 includes controller 320 which is implemented in the form of a controller such as the well-known and programmable PIC controller (model no. PIC16F877A). In anticipation of operation during power failure conditions controller 320 is powered by batteries 310 also contained within package 300. In response to a signal from angle sensor 200, controller 320 operates to shut off power to pump 215 through control of power switch 330. It is noted however that certain feeding pumps are provided with their own battery backup so that simply disconnecting these units from a source of electrical power does not actually prevent their continuing to function. In such cases, preferred embodiments of the present invention operate by detecting continued flow in the feeding tube 250 using flow sensor 370 which is preferably disposed in the same package 350 as actuator 360. Actuator 360 and flow sensor 370 represent portions of the present invention which are disposed adjacent to feeding tube 250 and which are preferably connected to the package 300 the a single electrical cable (unlike the units shown in FIG. 9 which are not intended to illustrate detailed physical configurations but rather functional configurations).

Figure 10:
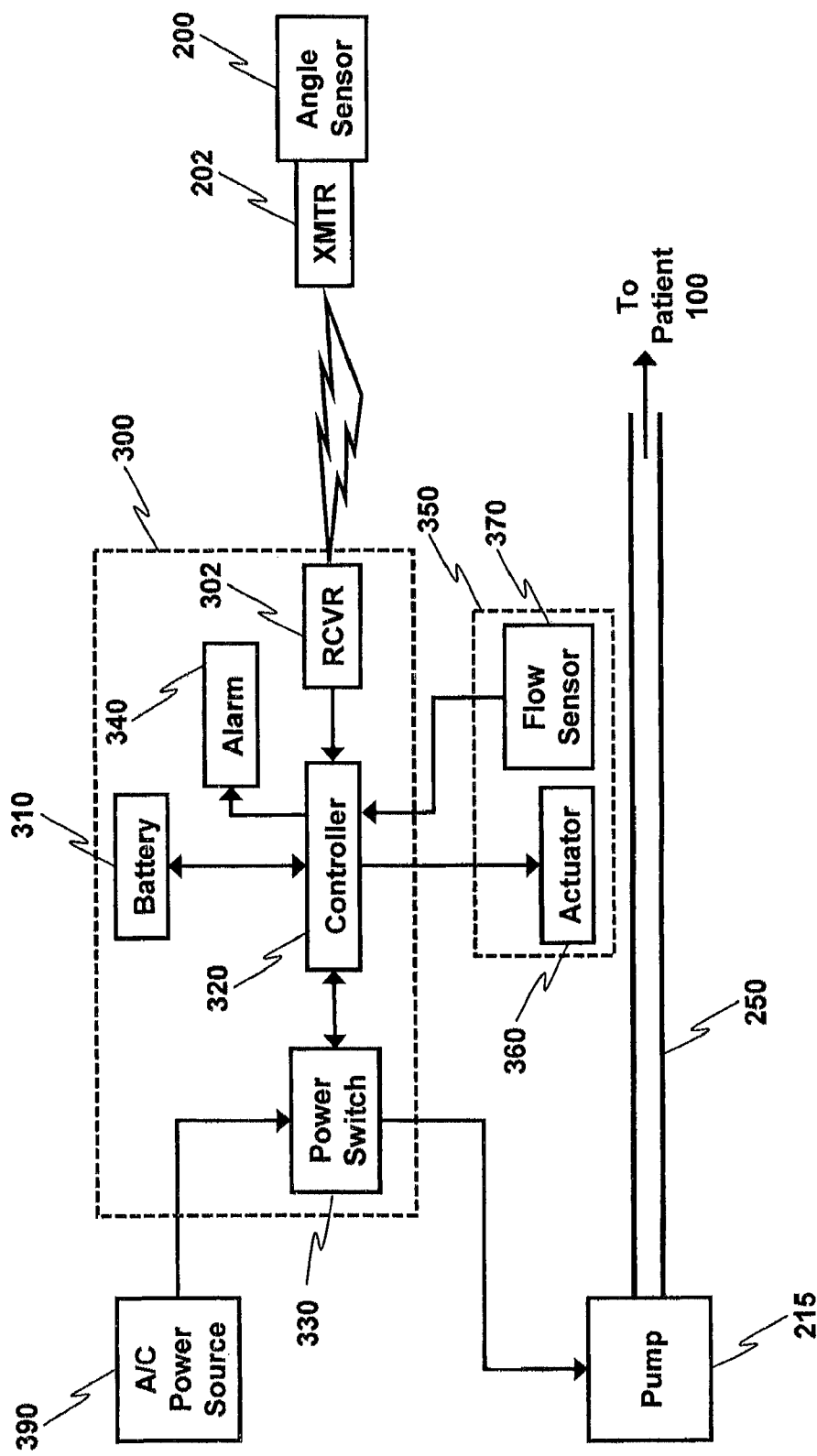

In the event that signals from angle sensor 200 to controller 320 indicate the presence of an improper angle or other patient positioning irregularity, controller 320 responds by causing actuator 360 to exert sufficient pressure on feeding tube 250 to prevent the continued flow of fluid therein. Flow sensor 370, which is optional, is employed in those circumstances where it is desirable to provide feedback to the controller of the present invention indicating that flow has indeed ceased. In some embodiments of the present invention, for use in those circumstances where it is known that a pump includes a battery backup, power switch 330 is either eliminated or simply bypassed with actuator 360 being relied upon to produce a cessation of fluid flow. This arrangement provides easy retrofit capabilities. An arrangement in which the feeding tube is cut and an electrically actuatable valve is inserted in the flow path also provides a retrofit capability but is not quite as convenient. As shown in FIG. 10, it is also possible to provide sensor 200 with wireless transmitter 202 and to likewise provide controller package 300 with wireless receiver 302. Package unit 300 and package unit 350 are also connectable in a wireless manner. In any event actuator 360 operates to cutoff fluid flow in tube 250 by mechanical intervention separate and apart from any operating modalities of the pump supplying the fluid.

In any event, as indicated elsewhere herein, the present invention also preferably includes an alarm function 340 being controlled by controller 320 in response to signals sent from angle sensor 200. Alarm 340 is either an audio alarm or a visual alarm or both. Additionally, alarm 340 also is capable of including wireless transmission functions capable of broadcasting either processed or raw information from angle sensor 200.

According to the description shown in FIG. 9, the following components provide the core components of the present invention which are easily integrated to provide the functionality described herein. In particular, there is included a dual axis accelerometer/inclinometer which provides a dual-axis acceleration and inclination angle measurement system packaged as an integrated circuit which is deployed to provide varying resolution of the patient's position relative to the Earth's horizon. The sensor is firmly affixed to the patient. Any convenient attachment method may be provided. For example, the sensor may be provided with an adhesive backing (temporary or otherwise) such as the adhesive that is employed with EKG electrodes. Alternatively, the sensor may be provided with an adjustable elastic loop which fits around the patient's chest or upper body. There is also included a microcontroller functioning as a dedicated controller which is deployed to enable the function of sampling input from the accelerometer/inclinometer and for controlling pump and alarm activity. Power relays, switches and communications components, which are driven by the microcontroller, attached relays and switches are used to stop, start, or change the pump's modality and trigger alerts based on monitored parameters and encoded heuristics. It is therefore seen that the present invention is capable of monitoring the duration of a significant event and is capable of responding accordingly. The patient may shift position for a brief period of time exceeding a threshold. The microcontroller is programmed to respond based on rules and logic that take into account variations in the patient's position as a function of time.

Is also seen that the present invention is capable of using as accelerometer/inclinometer's acceleration outputs as parameters that indicate the velocity of the patients change in position. If the acceleration the patient's position is sudden, an alarm is preferably triggered to alert hospital staff that the patient may have fallen; as indicated elsewhere herein this is an ancillary benefit of the present invention that exists in addition to controlling pump functions.

The specific angle sensing and feedback control mechanisms deployed herein are a function of the microcontroller chosen. In any event, the algorithm provided is employed to interpret changes in the patient's position and trigger one or more relays to activate a bed controller if desired or convenient. Any industry standard embedded microprocessor is employable to input and interpret analog or digital information provided by an accelerometer/inclinometer attached to a patient. Command and data transfer between the inclinometer (sensor) and the microprocessor are either wired or wireless. An algorithm is employed to provide varying responses to changes in the patient's position and control various attached components.

Figure 11:
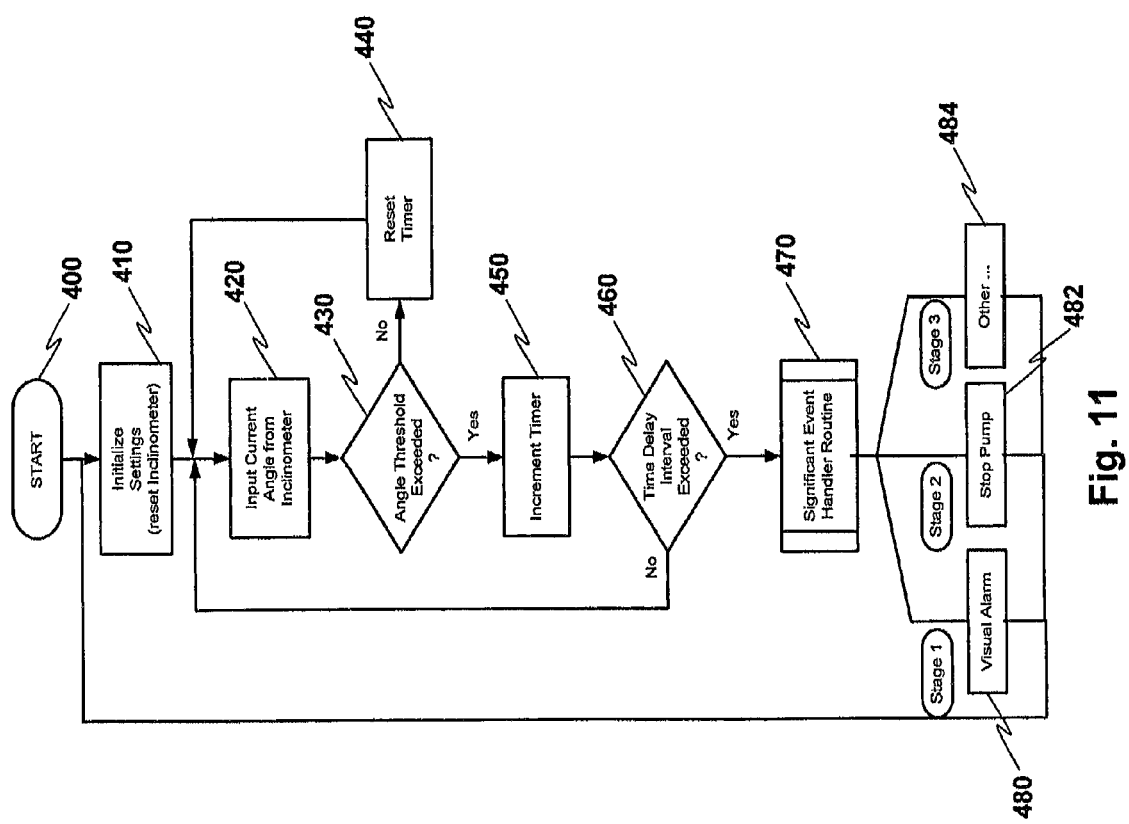
FIG. 11 is a process flow diagram illustrating an exemplary algorithm which implements one embodiment of the present invention.

Included in FIG. 11 is a sample process flow diagram that illustrates a possible primary use-case scenario for responding to significant events with respect to a patient's position as a function of time.

The patient's position and incline are continuously monitored by the microcontroller 320. Microcontroller 320 reads the X and Y tilt and acceleration vectors. Microcontroller 320 assesses these values against a predefined heuristic to manage the systems response to various events.

Positioning the sensor on the patient is accomplished by attaching the sensor to the patient's garment, on the shoulder or on the upper body. Positioning of the sensor is not critical. Once attached, microcontroller 320 is initialized to sense the current X and Y coordinates relative to the Earth's horizon as a baseline reference. All changes in the patient's position are interpreted relative to this baseline.

Microcontroller 320 is programmed to respond to multiple disparate events and inputs. Its primary role is to monitor and interpret changes in the patient's position as it continuously reads the position of the accelerometer/inclinometer (sensor). Microcontroller 320 is programmed to automatically control the pump and other discrete devices based on a heuristic algorithm which preferably emulates how an attending technician/care provider would manually responded to a similar significant event. Automatic pump shut-down, pump reversal (in those cases in which the control circuitry is linked with the design of the pump, as opposed to being retrofitted as provided herein), auto-recovery and graduated alerting of staff are all possible functions of microcontroller 320.

FIG. 11 illustrates an algorithm that is implemented by controller 320. The following steps are provided as part of a usable control procedure: Start: System switched on (step 400). Initialize Setting (Reset Inclinometer): Set baseline angle after affixing sensor to patient and initialize timer (step 410). Input Current Angle from Inclinometer: Request current X and Y axis positions from sensor 200 (step 420). Angle Threshold Exceeded?: If the current patient's incline is within tolerances, reset the timer (step 440) and request new input (step 420). Reset Timer: The timer is reset as the result of X and Y axis parameters are within normal range. If either the X or Y axis incline angle exceeds a limit indicating an abnormal condition, increment the timer (step 450). Time Delay Interval Exceeded?: (step 460) If the duration of the event did not exceed a time limit, return to step 420 and request new input from the sensor. If the timer (counter) has exceeded the acceptable time limit, the significant event handler routine (step 470) is invoked. Significant Event Handler Routine: The event handler routine is called if a significant event occurs requiring a corrective action or alert. A set of conditional statements evaluate key parameters, such as the severity of the angle of incline and the duration of the event to determine if one or more staged responses are indicated. Stage 1-Stage 3 (steps 480, 482 and 484): The event handler routine (step 470) selects the appropriate sub-routine for taking corrective action. Once remediation is complete, the system is reset (step 410).

Figure 12:
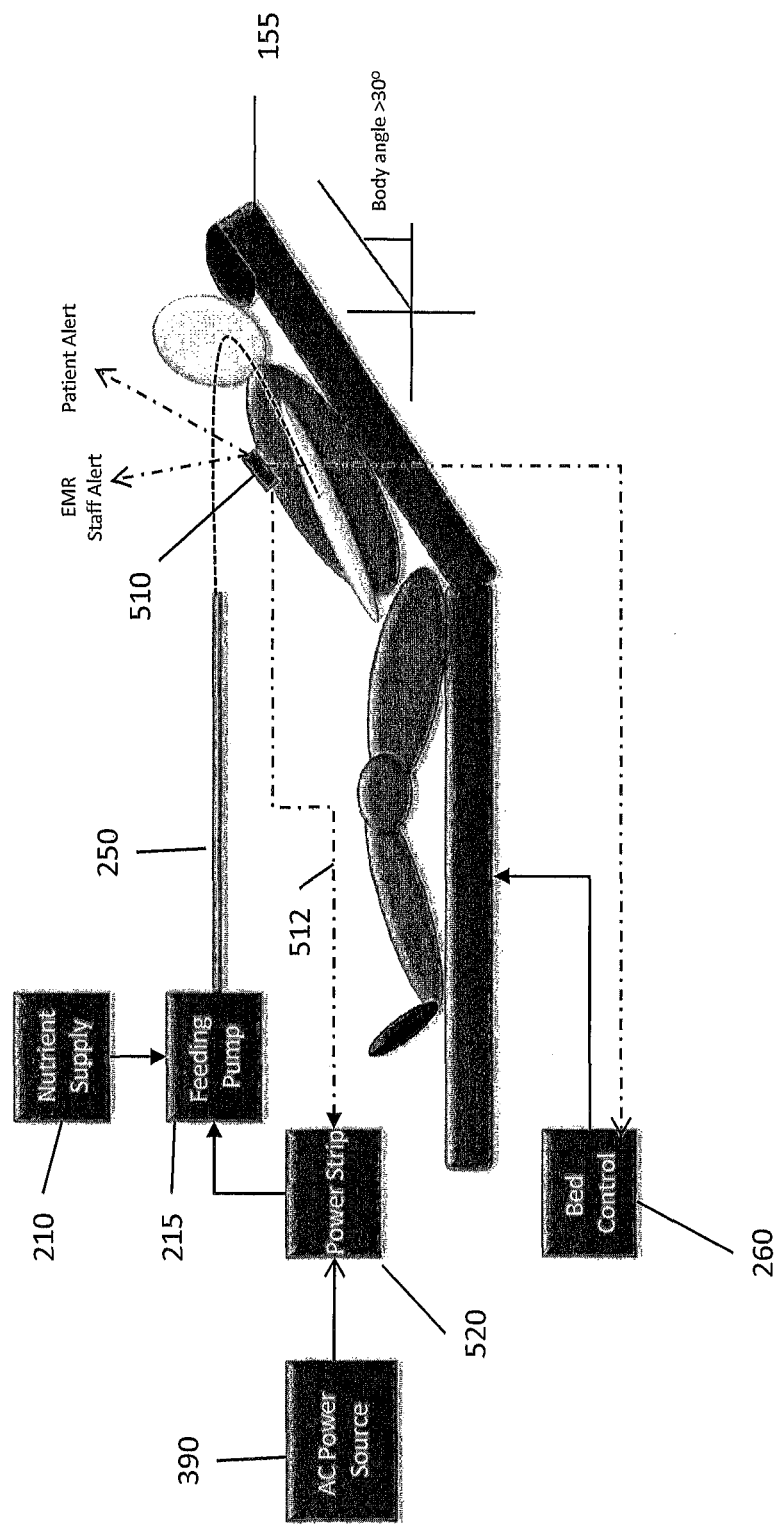
FIG. 12 is a block diagram illustrating an exemplary embodiment of the invention implemented with a smart phone application and a BLUETOOTH® controlled power strip.
Figure 13:
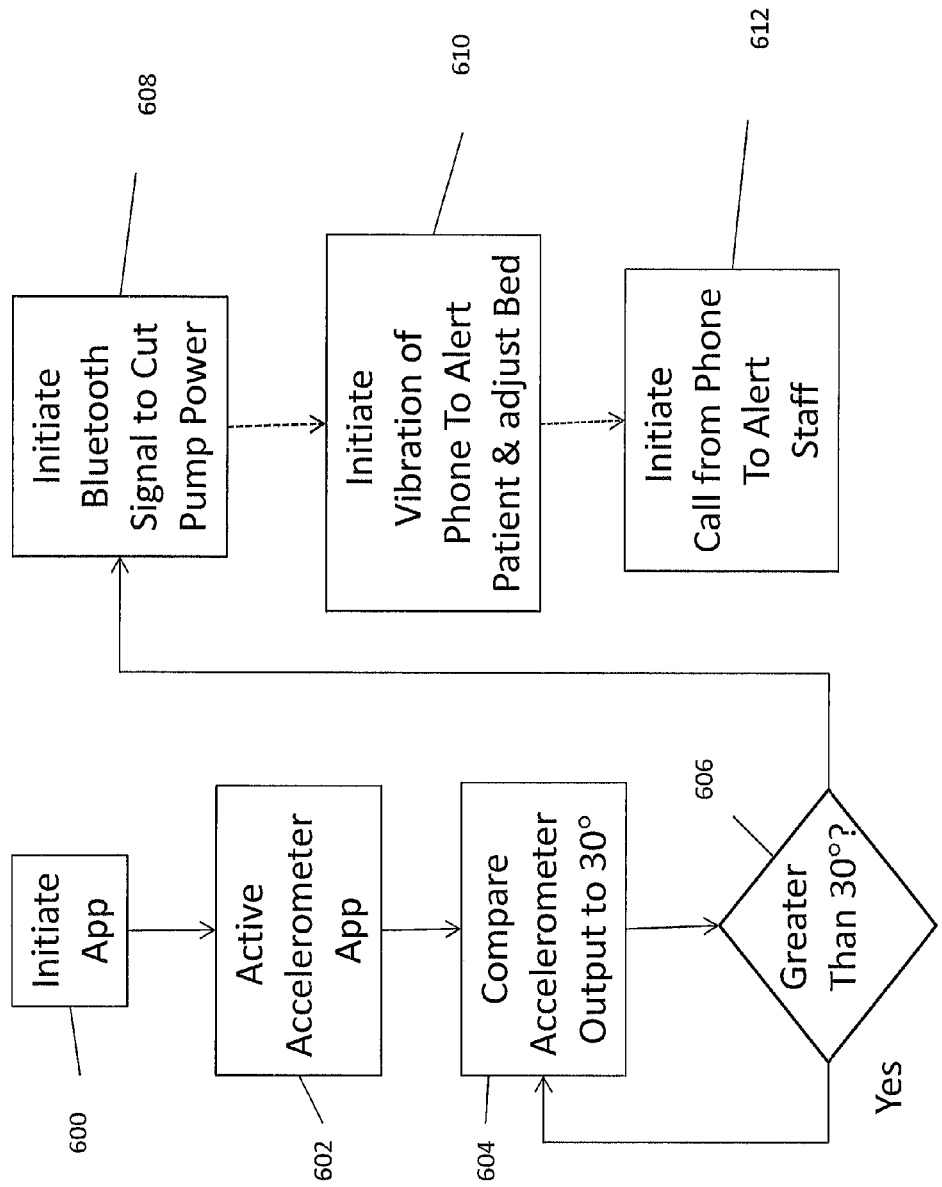
FIG. 13 is a flow chart of the exemplary algorithm which implements the smart phone embodiment of FIG. 12.

Another embodiment of the present invention utilizing a "smart phone," such as the APPLE® iPhone®, is shown in FIG. 12. The smart phone 510 can be attached to the chest of the patient, e.g., by placing it in a breast pocket of the patient's pajamas, by using VELCRO® to attach it to the patient's undershirt or a strap placed about the patient's chest, or by taping it directly to the patient's chest or a garment covering the patient's chest. The microprocessor of the smart phone 510 runs an aspiration prevention application that utilizes or invokes other applications that are run on the phone. In particular, inclination of the patient can be determined by an accelerometer/inclination device, e.g. an LIS302DL, which is provided in the phone and is operated by an application running on the smart phone, e.g. the Accelerometer Data Pro application. In order to implement the present invention, a second application is especially designed for the smart phone. This application, which is shown in FIG. 13, may be initiated in step 600 by the hospital staff. It in turn invokes the accelerometer/inclination application on the phone at step 602 and monitors the patient inclination information. Further, at step 604 it compares the inclination information with a set value or values. These values may be based on protocols established by the CDC, FDA or specialty organizations such as the American Gastroenterological Association, based on clinical data or they may be individual institutional protocols established by healthcare facilities. For example if it is determined that feeding of the patient should cease when his inclination is less than 30°, it may generate a warning signal at 35° and a cutoff signal at 30°. These values are stored in the smart phone and at the comparison step 604 it determines whether the patient's inclination has dropped below one of these values. If it has not, the program merely loops and continues to monitor the inclination. However, if it is determined that one or more of the preset values has been passed, then the application in step 608 invokes the BLUETOOTH® or other wireless circuitry in the phone in order to generate one or more signals in response thereto.

As shown in FIG. 12, the wireless circuit in the smart phone produces a wireless signal 512 that is received at the BLUETOOTH® controlled power strip 530. This power strip may, e.g., be based on the National Control Devices, 16-Channel BLUETOOTH® Relay Controller Boards. As shown, AC Power source 390 provides power to the strip. Under normal circumstances, this power passes through the strip to the feeding pump 215 that is plugged into the BLUETOOTH® controlled power strip. When the special application generates the BLUETOOTH® signal, power in the strip is cut off and the pump stops. As a result, the nutrient in nutrient supply 210 is no longer delivered through feeding tube 250 and patient aspiration is prevented.

Further, the special application in the smart phone may be optionally programmed to trigger an alarm in the smart phone to alert the patient. For example the patient may have drifted off to sleep and the alarm may be sufficient to awaken him and cause him to adjust his position in bed. The alarm may be activated by the special application invoking the audio and/or vibration circuits in the smart phone as shown in step 610 of FIG. 13. The fact that this function is optional is indicated in FIG. 13 by a dotted line between the power cutoff step 608 and the alarm step 610. If a member of the staff is reasonably close to the patient, e.g., in a neighboring room, the sound and/or vibration may be sufficient to attract their attention so they can assist the patient and restore proper feeding at the earliest time possible.

The BLUETOOTH® or other wireless signal may also be used to affect the bed control 260 as shown in FIG. 12. In such a case the bed control would need to be equipped with a BLUETOOTH® controller that would receive the signal and decode it into a bed command that would cause the movable head portion 155 of the bed to rise in an attempt to get the patient above the 30° angle position. This could be programmed to occur at a special time, e.g., at 35° when the patient's position has not yet reached the critical position, or it can be a part of the signal during step 610 after the patient has reached the critical angle as shown in FIG. 13. If programmed to issue a warning before the critical angle is reached, it would be likely that a significant number of pump shutoff conditions would be avoided due to intervention by the staff or the patient, or due to movement of the head of the bed.

It is possible that by activating the head of the bed in an attempt to raise the patient's angle, the patient will instead slide down in the bed. However, with the present invention this is not a problem because the inclinometer is on the chest of the patient so the actual orientation of the patient is known. As a result because the inclination signal falls below 30° despite the raising of the head of the bed, the pump will still be shut off. Further, the application could be programmed to halt any further increase in the head of the bed under such circumstances. Thus, the arrangement of the sensor on the patient is a significant advance over some suggested systems that rely solely on bed position.

While the local alarm on the smart phone can notify the staff of a feeding problem if they are close, it cannot notify them if they are at some distance away, e.g., at a nurse's station. As a further option the special application can invoke the phone circuits in the smart phone and cause them to place a phone call to a nurse's station. The application can even be programmed so that when the phone is answered at the nurse's station, it will cause a pre-recorded message to play that indicates that the pump has stopped, and even the location of the pump. In addition to contacting the nurse's station, the smart phone can communicate, e.g., by WiFi, with an Electronic Medical Record (EMR) system. Thus, the patient's electronic medical record and be automatically updated with information about interruptions in the patient's feeding schedule. This serves two functions. First, it acts as proof that the medical facility was in compliance with the policies of government, accrediting agencies or hospitals in that while the person was being feed they were at greater than 30°. Second, if the connection to the EMR system is with a two way communication device, the dietitian, doctor or other qualified person could monitor and program the pump.

This phone alarm feature and any of the ancillary alarms and operations (e.g., a change in the head of the bed position, can be programmed to operate before the patient reaches the critical angle. As a result, the patient, the staff and the bed position can all be alerted or operated to keep the patient from reaching the critical condition. Also, if the pump shut off signal is generated, and the inclination signal indicates that the patient has returned to a safe position, the special application can be programmed to send out another BLUETOOTH® signal that causes power strip 520 to reestablish power to the pump. Depending on its characteristics, this may allow the pump to turn on and feeding to resume, or it may at least allow for manual restarting of the pump. Where this function is not provided, the power strip will have to be manually reset.

While in one embodiment it is contemplated that an accelerometer/inclinometer application in the smart phone is utilized, it is also possible to use an external accelerometer/inclinometer sensor. In such a case the inclination signal from the external sensor would be provided to a microprocessor for evaluation. For example, it could be provided to the microprocessor of the smart phone. In such a case the sensor is attached to the patient, but the smart phone need not be attached to the patient, so long as it is sufficiently close to the sensor that it can receive an inclination signal from the sensor, e.g., wirelessly via BLUETOOTH® communications. The processor in the smart phone would then determine when the inclination signal indicated that the patient was at or near the critical angle and would generate a further signal in response. This further signal could be a BLUETOOTH® signal sent to the power strip from which the pump is receiving power so as to turn off the pump. It could also be an alarm signal.

In the embodiment of FIG. 12 it is contemplated that the system will employ the BLUETOOTH® controlled power strip to turn off the pump when the critical angle is reached. However, it is also within the scope of the invention to merely have the microprocessor activate an alarm without turning off the pump. In such an arrangement the wirelessly controlled power strip would not be necessary, and the system would include only the sensor and the smart phone. In fact, a useful device according to the present invention would merely be a smart phone application that signals when the patient's angular position is too low.

Smart phones are equipped with a significant amount of memory. This allows the system to store information on its operation and the patient. For example the phone could make a record of every time the patient's position goes below 35° and/or 30°. It could also record whether the pump was stopped and the amount of time until a pump start signal was generated. The collection of such information would be beneficial in further development of the system and improving patient care procedures.

If the pump is shut off and not restarted for a period of time, there could be a problem in that the patient will not receive the proper amount of nourishment. However, by using volume based feeding, this issue can be addressed. In particular, if the total volume is calculated and entered into the pump, it may adjust for the off time. If an existing pump does not have this feature, it can be programmed into the processor of the smart phone. For example the processor of the smart phone could track the "on time" for a pump. In the event of a shutdown, it could provide a message on its screen as to how much additional time the pump must be set to after it is restarted in order to make up the prescribed volume of nourishment.

Even if this additional feature is not provided, its absence will have a different impact under different situations. In particular, the average times that the pump would be off will differ by the healthcare environment. The intensive care unit (ICU) with its low patient to staff ratio, would have off times that would likely be less than 1 to 5 minutes. On a medical floor with an average staffing ratio of 7 to 1, the pump could be off as much as 15 to 30 minutes. In the home setting, where the patient or a family member may have to manage the feeding, the off time is likely to be short. In a long term care situation the off time could be significantly longer, e.g., 30 to 120 minutes. These feeding off times are not likely to impact overall patient outcomes when compared to the benefit derived from avoiding aspiration pneumonia.

The issue of pump shut off time having an effect on the total nutrition received by the patient may also depend on the patient's condition. For example, you do not want the pump to be off too long or at all where a diabetic patient is being given insulin. There may be other diseases where this is the case. However, this must be balanced against the possibility of aspiration pneumonia. One way to address this is to modify the software so that instead of cutting off power to the pump, the signal only activates an alarm.

The operation of the microprocessor and applications of the smart phone as set forth in FIGS. 12 and 13 could be rendered in an especially designed device that has only necessary or desired optional features of a smart phone. Also, other features of the smart phone can be invoked either as part of the use of the phone or as separate especially designed devices. As an example smart phone are typically equipped with GPS circuits. These may be used to locate a patient in a hospital, e.g., when the patient is out of his room for tests. In addition, if the patient is ambulatory, the GPS circuits may be used to assist the patient in finding various locations in the hospital.

While the invention has been described in detail herein in accordance with certain preferred embodiments thereof, many modifications and changes therein may be effected by those skilled in the art. Accordingly, it is intended by the appended claims to cover all such modifications and changes as fall within the spirit and scope of the invention.

I claim:

1. A device to prevent aspiration of gastric fluids by a patient being fed or medicated through a gastric tube connected to a feeding pump, said device comprising:
    an angle sensor capable of being affixed to an external portion of a chest of the patient, said sensor providing an angular electrical signal indicative of the sensor's angular position;
    an electrical control circuit that receives said angular signal and compares it to a threshold angle, said electrical control circuit generating a wireless control signal when the angular signal indicates a position of the sensor lower than the threshold; and
    a power switch that controllably supplies power to the feeding pump, said power switch receiving said wireless control signal and turning off power to the feeding pump in response to receipt of the wireless control signal, whereby material in the gastric tube is caused to stop flowing.

2. The device of claim 1 wherein the wireless control signal is communicated to an electronic medical record system and is associated with the patient's medical record.

3. The device of claim 1 wherein the angle sensor and the electrical control circuit are separate units and the angular signal is wirelessly transmitted to the electrical control circuit from the angle sensor.

4. The device of claim 1 wherein said electrical control circuit further generates a secondary control signal when the angular signal indicates a position close to, but above the threshold angle to sound an alarm that warns of impending aspiration, and the angular threshold and the position close to, but above the threshold are set based on individual instructional protocols.

5. The device of claim 4 wherein the angular threshold is 30° and position close to, but above the threshold angle is 35°.

6. The device of claim 1 wherein the patient is reclining in a bed with a head part that is angularly adjustable by a bed position control circuit, wherein said electrical control circuit further generates a secondary control signal when the angular signal indicates a position close to, but above the threshold angle, said secondary signal causing said bed position control circuit to cause the head part of the bed to rise in an effort to keep the angular signal from reaching the threshold angle.

7. The device of claim 6 wherein the secondary control signal received by the bed position control circuit is a wireless signal.

8. The device of claim 1 wherein the electrical control circuit includes memory and a display, and wherein the electrical control circuit keeps track of the time during which the pump is off by measuring the time and accumulating it in the memory, said electrical control circuit further displays the accumulated off time on the display.

9. The device of claim 8 wherein said electrical control circuit further generates a secondary control signal when the angular signal indicates a position close to, but above the threshold angle, and the electrical control circuit further keeps track of times when the wireless control signal and the secondary control signal are generated and accumulates them in the memory, said electrical control circuit further displays the accumulated control signal times on the display.

10. The device of claim 1 wherein said angle sensor and control circuit are applications running on a microprocessor of a smart phone that includes an accelerometer/inclinometer device.

11. The device of claim 10 wherein said wireless control signal is a BLUETOOTH® signal generated by said smart phone and said power switch is controllable by receipt of said BLUETOOTH® signal.

12. The device of claim 10 wherein said smart phone is affixed to the patient by at least one of placing it in a breast pocket of a garment worn on the upper body of the patient, using VELCRO® to attach it to a garment worn on or a strap located about the chest of the patient and taping it to the chest of the patient or a garment worn on the upper body of the patient.

13. The device of claim 10 wherein said smart phone further includes a mobile telephone circuit and wherein said electrical control application invokes the telephone circuit upon generation of the wireless control signal, said special application causing the telephone circuit to dial a pre-assigned number and to deliver a prerecorded message when the dialed number answers.

14. The device of claim 10 wherein said smart phone further includes an alarm and wherein said control circuit application generates a secondary control signal when the angular signal indicates a position close to, but above the threshold angle, said secondary signal causing said alarm to activate.

15. The device of claim 14 wherein the alarm is at least one of an audible alarm and a vibration alarm.

16. A device to prevent aspiration of gastric fluids by a patient being fed or medicated through a gastric tube connected to a feeding pump, said device comprising:
    a smart phone that includes a microprocessor and an accelerometer/inclinometer device, said smart phone running an inclinometer application on its microprocessor that provides an angular electrical signal indicative of the phone's angular position, said smart phone being attachable to an external portion of a chest of the patient, said smart phone further running an electrical control application on its microprocessor that receives said angular signal and compares it to a threshold angle, said electrical control application invoking a wireless control signal when the angular signal indicates a position of the sensor lower than the threshold angle; and
    a power switch that controllably supplies power to the feeding pump, said power switch receiving said wireless control signal and turning off power to the feeding pump in response to receipt of the wireless control signal, whereby material in the gastric tube is caused to stop flowing.

17. The device of claim 16 wherein the wireless control signal is communicated to an electronic medical record system and is associated with the patient's medical record.

18. The device of claim 16 wherein said smart phone further includes a mobile telephone circuit and wherein said electrical control application invokes the telephone circuit upon generation of the wireless control signal, said electrical control application causing the telephone circuit to dial a pre-assigned number and to deliver a prerecorded message when the dialed number answers.

19. The device of claim 16 wherein said wireless control signal is a BLUETOOTH® signal generated by said smart phone and said power switch is controllable by receipt of said BLUETOOTH® signal.

20. The device of claim 16 wherein said smart phone is affixed to the patient by at least one of placing it in a breast pocket of a garment worn on the upper body of the patient, using VELCRO® to attach it to a garment worn on, or a strap located about, the chest of the patient and taping it to the chest of the patient or a garment worn on the upper body of the patient.

21. The device of claim 16 wherein said electrical control application further generates a secondary control signal when the angular signal indicates a position close to, but above the threshold angle.

22. The device of claim 21 wherein the angular threshold is 30° and position close to, but above the threshold angle is 35°.

23. The device of claim 16 wherein said smart phone further includes an alarm and wherein said electrical control application generates a secondary control signal when the angular signal indicates a position close to, but above the threshold angle, said secondary signal causing said alarm to activate to warn the patient or attending staff of impending aspiration of gastric fluids and or pump shut off.

24. The device of claim 23 wherein the alarm is at least one of an audible alarm and a vibration alarm.

25. The device of claim 16 wherein when the patient is reclining in a bed with a head part that is angularly adjustable by a bed position control circuit, said electrical control application further generates a secondary control signal when the angular signal indicates a position close to, but above the threshold angle, said secondary signal causing said bed position control circuit to cause the head part of the bed to rise in an effort to keep the angular signal from reaching the threshold angle.

26. The device of claim 25 wherein the secondary control signal received by the bed position control circuit is a wireless signal.

27. The device of claim 16 wherein the smart phone includes memory and a display, and wherein the electrical control application keeps track of the time during which the pump is off by measuring the time and accumulating it in the memory, said electrical control application further displays the accumulated off time on the display.

28. The device of claim 27 wherein said electrical control application further generates a secondary control signal when the angular signal indicates a position close to, but above the threshold angle, and the electrical control application further keeps track of the times when the wireless control signal and the secondary control signal are generated and accumulates them in the memory, said electrical control application further displays the accumulated control signal times on the display.

* * * * *